(12) United States Patent
Mellert et al.

(10) Patent No.: US 7,145,350 B2
(45) Date of Patent: Dec. 5, 2006

(54) PROCESS AND A CIRCUIT ARRANGEMENT FOR EVALUATING A MEASURING CAPACITANCE

(75) Inventors: Martin Mellert, Steinach (DE); Jürgen Fichter, Schiltach (DE); Herbert Auber, St. Georgen (DE)

(73) Assignee: Vega Grieshaber KG, Wolfach (DE)

( * ) Notice: Subject to any disclaimer, the term of this patent is extended or adjusted under 35 U.S.C. 154(b) by 0 days.

(21) Appl. No.: 10/885,514

(22) Filed: Jul. 7, 2004

(65) Prior Publication Data

US 2005/0104604 A1    May 19, 2005

(30) Foreign Application Priority Data

Jul. 22, 2003    (DE) ................. 103 33 154

(51) Int. Cl.
*G01R 27/26* (2006.01)

(52) U.S. Cl. ............... 324/678; 324/664; 324/686; 324/689; 324/658; 324/665

(58) Field of Classification Search ............... 324/678, 324/663, 664, 689, 677, 711, 658, 686
See application file for complete search history.

(56) References Cited

U.S. PATENT DOCUMENTS

| | | | | |
|---|---|---|---|---|
| 5,150,059 A | * | 9/1992 | Bognar et al. ............. | 324/551 |
| 5,461,321 A | | 10/1995 | Sanders et al. | |
| 6,020,744 A | * | 2/2000 | Ghorashi et al. .......... | 324/678 |
| 6,191,723 B1 | * | 2/2001 | Lewis ....................... | 341/166 |
| 6,250,152 B1 | * | 6/2001 | Klein et al. ............... | 73/304 C |
| 6,509,746 B1 | * | 1/2003 | Wang ........................ | 324/678 |
| 6,731,121 B1 | * | 5/2004 | Hsu et al. .................. | 324/678 |
| 6,768,319 B1 | * | 7/2004 | Wang ........................ | 324/679 |
| 6,853,201 B1 | * | 2/2005 | Hirn et al. ................. | 324/678 |

FOREIGN PATENT DOCUMENTS

| | | |
|---|---|---|
| CN | 1041457 A | 4/1990 |
| CN | 1111355 A | 11/1995 |
| CN | 1266494 A | 9/2000 |
| DE | 42 22 788 A1 | 1/1994 |
| DE | 43 40 472 C1 | 4/1995 |
| DE | 4340472 C1 * | 4/1995 |
| DE | 10028353 A1 * | 12/2001 |
| EP | 1 411 349 A1 | 4/2004 |
| WO | WO 01/04648 A1 | 1/2001 |

* cited by examiner

*Primary Examiner*—Anjan Deb
*Assistant Examiner*—Marina Kramskaya
(74) *Attorney, Agent, or Firm*—Nath & Associates; Jerald L. Meyer; Matthew J. Moffa

(57) ABSTRACT

A process is disclosed for evaluating a measuring device comprising a capacitor (CM), with stages for charging the capacitor (CM) over an initial charging period (tk1, tk2) and for determining the capacitance charge as an initial measured value (tm1). To determine a measuring condition that changes a normal state of the capacitance, e.g., moist as opposed to dry surroundings for the measuring cell, the process exhibits the following additional steps: charging the capacitance (CM) over a second charging period (tk2), which differs from the first charging period (tk1); determining the charge of the capacitance (CM) as a second measured value (tm2); and comparing the first and second measured values (tk1, tk2) to establish the comparative result.

18 Claims, 4 Drawing Sheets

PROCESS AND A CIRCUIT ARRANGEMENT FOR EVALUATING A MEASURING CAPACITANCE

BACKGROUND OF THE INVENTION

1. Field of the Invention

The invention relates to a process for evaluating a measuring capacitance in accordance with the preamble of claim 1, as well as to a circuit arrangement for implementing this process.

2. Description of the Related Art

A process for measuring a capacitance is known, e.g., from DE 34 13 849 A1 and from DE 35 44 187 A1. In the first of these publications, FIG. 1 shows a circuit arrangement for measuring a capacitance, in which the capacitance is maintained permanently at a reference potential by an electrical connection and the other connection is switched between a reference voltage source and an integrator. The circuit contains an integrating device, which is connected to an operating voltage and exhibits an operational amplifier. The integrating device is charged with the charge of the capacitance being measured and is then discharged by means of a circuit device lying parallel to an integrating capacitor. The characteristics of the recharging process are a measure of the capacitance being measured.

The second publication describes a capacitance measuring circuit which also exhibits a switching arrangement, one that applies a constant voltage to the measuring capacitance, with a predetermined switching frequency which changes periodically for the purpose of charging, and for the purpose of discharging connects the measuring capacitance to a storage capacitor, whose capacitance is large compared to the measuring capacitance. The terminal voltage of the storage capacitor is basically held to a constant reference potential by a controlled discharge current. In contrast to the first publication, the measure of the capacitance being examined is not the recharging frequency, but the magnitude of the discharge current in proportion to the measuring capacitance.

A process for measuring the capacitance of capacitive sensors is also known from DE 42 37 196 C1. A connection for the capacitance being measured, i.e., for the measuring capacitor, is firmly attached to a reference potential, ideally the measuring potential of the entire configuration. Attaching a connection for the capacitance being measured to the reference potential is advantageous when the sensor is employed in undefined, variable conditions with respect to capacitance, for example, as caused by variable surface moisture or electrical couplings that create interference. Here the measuring capacitor electrode that faces the housing, or the medium under investigation, is kept at a constant potential. The other electrode of the measuring capacitor in this known circuit arrangement is connected, in a manner that permits switching, to the entrance of an integrating device that exhibits an integrating capacitor. The capacitance being measured is first charged in a charging phase by a predetermined potential difference, and then, in a discharging phase, the charge thus stored is recharged to the integrating capacitor of the integrating device and is evaluated there. In the process, the connection of the capacitance being measured that is not in contact with the reference potential is attached, in both the charging phase and the discharging phase, to a reference potential which is set to a different value in the charging phase than in the discharging phase. With a working voltage potential thus changing periodically, circuit arrangement capacitances that falsify the data are neutralized, and small capacitance values or changes can be evaluated with a high degree of accuracy.

The change-over of the operating voltage potential remains problematic in these known processes, however, and this can lead to difficulties, most of all when the circuit arrangement is realized as an application-specific integrated circuit (ASIC) in CMOS technology, since here the different operational voltage potentials must be controlled on a single ASIC substrate.

To be sure, the measurement of a capacitance in a case where one connection is firmly attached to the reference potential is characterized by a lower sensitivity to other interference effects; however, it is disadvantageous because of the inclusion of parasitic capacitances lying parallel to the precision capacitor. Such parasitic capacitances are not stable over time, nor are they stable with respect to temperature, and this also compromises the measuring results. Finally, resistances lying parallel to the precision capacitor also influence the measuring results. Although highly resistive, these parallel resistances arise due to surface coatings on sensor ceramic substrates, as caused by moisture in the air.

In this connection, DE 43 40 472 C1 proposes a process and a circuit arrangement for measuring the capacitance of a precision capacitor, where one connection is firmly attached to the reference potential; the arrangement can be realized on a single ASIC substrate and allows interference effects caused by parallel resistances to be reduced. The publication specifies a process for measuring a capacitance whose first connection is attached to the reference potential; an integrating device is employed which is connected to an operating voltage and which exhibits a integrating capacitor that is charged with the charge of the capacitance being measured and is then discharged, such that the recharging frequency represents a measure of the capacitance under investigation and such that the integrating capacitor in each case is charged and discharged up to a predetermined reference threshold, and at the beginning of the charging or discharging event negative or positive charging surges with equal amplitudes are transferred to the integrating capacitor by coupling with the capacitance (CM).

BRIEF SUMMARY OF THE INVENTION

The invention is based on the problem of improving a process and a circuit arrangement for evaluating the measuring capacitances of a pressure measuring device, which process and arrangement allow the stability of the measuring conditions to be monitored in a simple manner.

The preferred process for evaluating a measuring capacitance as the capacitance of a measuring device exhibits a first cycle of steps, in which the capacitance is charged in an initial charging period, which is understood to include the application of a negative charge, i.e., a discharge, whereupon the charge of the capacitance is determined as an initial measured value. Then the cycle is repeated over a second charging period, to determine a second measured value, whereupon the first and second measured values are compared in order to arrive at a comparative result, which serves to ascertain a measuring condition that may have modified the normal state of the capacitance and may thus potentially lead to a falsified result.

A preferred circuit arrangement for implementing this process in turn exhibits a measuring capacitance for determining a measured value, a charging and discharging circuit arrangement for charging and discharging the measuring capacitance, proceeding from a reference voltage, a measured value determinator for determining a measured value, and an evaluating device for evaluating the measured value. The individual circuit components for determining two different measured values are formed by the application or withdrawal of charges to the capacitance, with differing charging and discharging periods. The individual components can take the form of separate circuit components or can be partially or entirely designed as an integrated circuit.

Advantageous elaborations are the subject matter of dependent claims.

Ideally the charging or discharging of the capacitance will be performed by recharging from or to another capacitance, proceeding from a reference voltage value of the other capacitance. Ideally the other capacitance is part of an integrating circuit, which after recharging performs a linear discharge or return charge of the other capacitance, until the value of the reference voltage is reached. The length of the discharge or return charge is established as the first or, as the case may be, the second measured value and stands in a direct relation to the measuring capacitance, and to the measuring condition to which the measuring capacitance is subject. The measuring condition, particularly dry or wet surroundings, can be directly inferred from the recharging period, which includes—in addition to the discharge or return charging process—the actual recharging between the two capacitances; or it can be directly inferred from the recharging cycle.

To take tolerances into account, a tolerance value can be expediently established, and predetermined value areas can be indicated, for comparison with the comparative result in order to determine an amount of change in the measuring condition.

It is useful to establish the first and second charging periods in such a way that a complete charge of the measuring capacitance is performed in a charging period, or a complete recharge between the measuring capacitance and the other capacitances. A complete charge is also understood to include an almost complete charge, bearing in mind that during the charging process a capacitor is subject to an exponential function over time. The other charging period is so selected that when the measuring conditions have changed an incomplete charge, or discharge or recharge, of the measuring capacitance occurs, so that the momentary measuring condition can be inferred from the differing first and second measured values.

When the comparative result is not reached or is exceeded by a predetermined threshold value it is useful to allow a warning signal to be given or to occasion an automatic correction of the measuring results.

Preferred areas of application are the determination of a moisture-conditioned change in the measuring capacitance and/or the determination of a change in the capacitance based on modified internal resistances on the capacitance charging path.

Ideally the process and the circuit arrangement will be realized on the basis of a process and a circuit arrangement with the known features of DE 43 40 472 C1, such that the entire contents disclosed there are completely taken over and converted for the purposes of the present invention.

An exemplary embodiment is next described on the basis of a drawing, whose figures show:

DETAILED DESCRIPTION OF THE INVENTION

Figure 1:
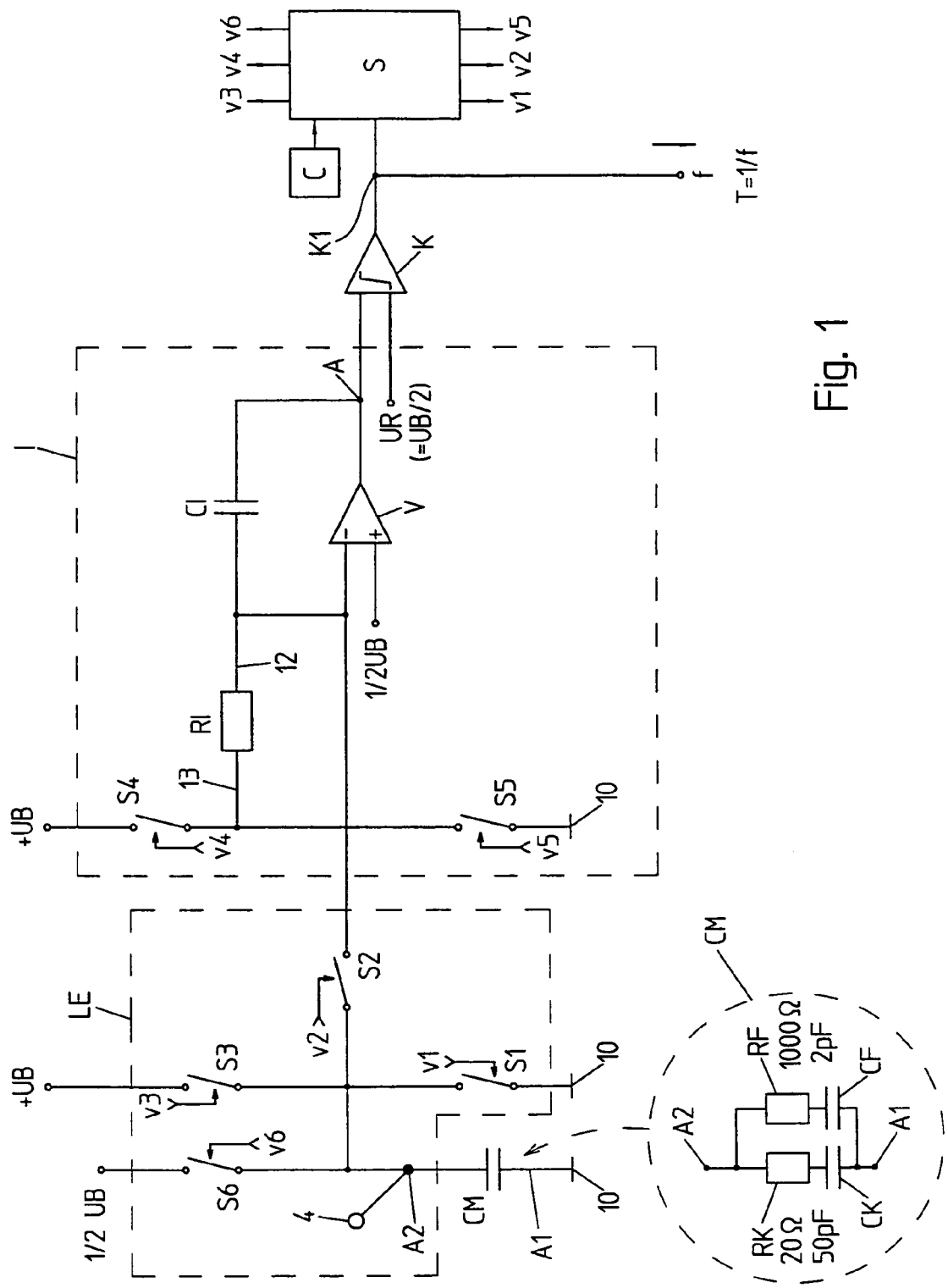
FIG. 1 a basic circuit diagram of a circuit arrangement for determining a measuring capacitance and evaluating the measuring condition FIG. 2 a measuring curve for voltage at an integrator outlet, and a depiction over time of the circuit states of various circuit components for a first predetermined recharging time, given ideal measuring conditions FIG. 3 a measuring curve for voltage at an integrator outlet for a second recharging period, given ideal measuring conditions FIGS. 4A, 4B voltage curves at an interfering capacitor lying parallel to the measuring capacitor, for the first and second recharging periods FIGS. 5A, 5B the corresponding measuring curves for voltage at the integrator outlet FIG. 6 the measuring curves of FIGS. 5A, 5B in a superimposed depiction with corresponding time bars

As can be seen from FIG. 1, a circuit arrangement with a measuring capacitance CM, exhibits a charging and discharging device LE, an integrating circuit I connected to it, a comparator K, a control device S for controlling the charging and discharging device LE and, if so desired, the integrator circuit I, and a frequency outlet f for issuing a frequency f. The individual components may partially or entirely consist of separate, individual structural units, as elements grouped on a printed circuit board, or may take the form of an integrated circuit.

The circuit arrangement serves specifically as a level or pressure gauge, with a capacitive pressure gauge cell as the capacitance CM to be measured. The evaluation of the capacitive pressure gauge cell proceeds in a known manner, for example according to the description given in DE 43 40 474 C1, whose content is incorporated in the embodiments here.

The evaluation of capacitance as the measuring capacitance CM or the reference capacitance, is modified from the known description in such a way that in addition to ascertaining the measuring capacitance CM or the reference capacitance, there is also an evaluation of the measured value or, as the case may be, of the measuring conditions which influence the measured value. In order to evaluate the measured value, the measuring capacitances—in the present case, the capacitance CM being measured and an integrating capacitance CI that can be coupled to it—are ascertained with two different recharging periods for recharging the charges between the two capicitances. If the measured values for the two reloading periods differ within established limiting values, this suggests an unstable measured value. The measured value can still be released as valid, however. If the limiting values are not reached or are exceeded, imprecise measured values must be assumed and an error signal released, or an automatic correction must be made. As a feature of the attendance operation of the system, a reliability value can be advantageously displayed, i.e., as a percentage indication of measuring uncertainty.

A measuring condition that must be particularly emphasized and which, upon modification, has a direct effect on the measured result or measured value is that of moisture in the area of the capacitance under investigation. Relative capacitive pressure gauge cells, in particular, can react sensitively to moisture. Moisture brings about a change in the effective capacitance values of the capacitance CM being measured. The effect of moisture is depicted in the sectional enlargement of FIG. 1. Positioned between two connections or taps A1, A2 is a capacitive measuring cell, with the capacitance CM that is being measured. Given dry measuring conditions, the effective feature here is a series connection consisting of a capacitive element CK and an ohmic element RK. If moisture is present, it has the effect of a parallel series connection consisting of another moisture-dependent capacitive element CF and a moisture-dependent ohmic element RF.

Taking as an example a pressure gauge under dry measuring conditions, the capacitance CK is, e.g., 50 pF and the internal resistance RK is 20 $\Omega$. With moist ventilation of the measuring cell the other parallel RC member is added to the actual measuring capacitance. The values for this parallel RC member can be, e.g., RF 1000 $\Omega$ for the internal resistance and 2 pF for the capacitive effect, although these values can vary within narrow boundaries.

For determining the value of the capacitance CM being measured the circuit arrangement exhibits an additional or other capacitor, which as an integrating capacitance CI is a component part of the integrator I. A timed recharging of the charges is effected between these two capacitors or capacitances CM and CI through actuation of a circuit S2. The voltage of the integrating capacitance CI changes between the individual reloadings, and a frequency signal f is released when a reference voltage UR is reached. Using the variation in recharging times between the capacitance CM being measured and the integrating capacitance CI, it can be determined whether or not a moisture-dependent component is present, namely by observing the measured values, or the frequency of the signal f, and examining them for different frequency values.

The two selected reloading times tk1, tk2 are chosen in such a way that for ideal, specifically, dry conditions the measuring capacitor CM is completely charged. Both recharging periods tk1 and tk2 lead to the same measuring result, or the same frequency value f.

Moreover, the two recharging times tk1, tk2 are so chosen that in the case of a moisture-dependent component which leads to a modified measuring condition, the measuring capacitor CM is completely recharged in the shorter recharging period, while for the longer recharging period the moisture-dependent component predominantly affects the total capacitance CM and is incorporated into the result.

For a typical recharging time of tk1=10 µs, 99% of the moisture-dependent component will enter the outcome, i.e., the entire 2 pF are included in the result. The moisture-dependent component with the time constant $\tau$=1000 $\Omega$·2 pF=2 µs as the time constant of the RC circuit, on the other hand, influences the result for a shorter reloading time tk2=3.3 µs by about 50%·2 pF, since the moisture-dependent capacitance value CF=2 pF for the capacitor is only about 50% charged, or recharged. The regular component of the capacitance CM being measured exhibits a time constant $\tau$=20 $\Omega$·50 pF=1 ns, with the result that the measuring capacitor CI in the short recharging period is only completely charged when dry measuring conditions are present.

As an alterative to the moisture-dependent component as a possible source of interference on capacitive pressure gauge cells, or in addition thereto, the connection resistances or internal resistances for the measuring capacitors may also be subject to a change which can lead to a falsification of the measured value. This too will manifest itself simply, in that the measured results, i.e., the periodic length of the frequency signal f for the two recharging times, are not identical.

The exemplary circuit arrangement is based on the circuit arrangement known to the prior art from DE 43 40 472 C1. In that publication, negative or positive charging surges of the same amplitude are transferred to the integrating capacitor of the integrating device at the beginning of the charging or discharging process by coupling the capacitance being measured. The integrating capacitor is then charged or discharged up to a predetermined reference threshold.

The essential advantage of the process rests in the elimination of interference effects from resistances lying parallel to the measuring capacitor—an advantage which makes the process particularly suited in measuring the capacitance of capacitive sensors—e.g., pressure gauges, temperature sensors, and the like—for which only a very small usable change in capacitance must be detected, and with a high degree of accuracy. The process is characterized by the fact that for any resistances parallel to the measuring capacitor the integration time constant is lowered in the ascending integration, i.e., during charging of the integrating capacitor, and this reduction is compensated for by an increase in the integration time constant in the descending integration and thus in the discharge of the integrating capacitor.

The process know from DE 43 40 472 C1 is implemented in the following specific stages: complete discharge of the capacitance being measured; charging the capacitance to half the operating voltage via the integrating capacitor of the integrating device; uncoupling the capacitance being measured from the integrating device and recharging the integrating device until a predetermined reference voltage applies at the outlet of the integrating device; application of the full operating voltage to the capacitance; discharging the capacitance to half the operating voltage using the integrating device, and consequent loading of the integrating device.

In a further elaboration, the capacitance being measured is only intermittently connected to the integrating device. Ideally the capacitance being measured will be connected to the integrating device for only about 0.05 (5 percent) of the cyclical period of the recharging frequency of the integrating capacitor. As a result, non-operate currents to the measuring capacitor caused by parallel resistances are able to influence the integrating capacitor for only a fraction of the measuring period.

According to the process, equally large positive and negative charging currents at the entrance of the integrating device alternate with the rhythm of the charge transfers. As a result, non-operate currents, which are caused by resistances occurring parallel to the measuring capacitor, withdraw from the integrating capacitor precisely as much charging current in the first half of the measuring period as the excess they have fed to the integrating capacitor in the second half.

In a further elaboration of the invention there is a reference capacitance connected parallel to the capacitance being measured; it is measured alternately with the measuring capacitance and is set in relation the latter in order to obtain a linear measured value.

In addition, a compensating capacitor can be provided that is connected parallel to the measuring capacitor during the measuring process and is applied to the full operating voltage in periods during which the measuring capacitor is discharged. As a result, the integrating period is reduced and the sensitivity of the entire measuring arrangement is enhanced.

In the basic circuit diagram of a circuit arrangement for measuring a measuring capacitance, as depicted in FIG. 1, a capacitance CM must be measured. This capacitance CM exhibits an initial connection A1 connected to reference potential 10, and exhibits a second connection A2. The capacitance being measured can be charged and discharged by means of a charging/discharging device LE. The charging/discharging device LE will typically exhibits three switches S1, S3, and S6, i.e., a first, a third, and a sixth switch S1, S3, S6. The first switch S1 is connected parallel to the capacitance CM, while the two other switches S3 and S6 are connected in series to the capacitance CM. The third switch S3 lies between operating voltage UB, which is full relative to the reference potential 10, and the second connection A2 of the capacitance being measured CM; the sixth switch S6 lies between this second connection A2 and a connection for half the operating voltage ½ UB.

In addition, an integrating device I is provided, with an integrating capacitor CI. In the circuit diagram shown in FIG. 1, the integrating device I exhibits an amplifier V with an inverting and a non-inverting entrance. The integrating capacitor CI is connected between the inverting entrance and an amplifier outlet, at which an outlet signal A can be read off.

The inverting entrance is additionally connected by a switching device—in this case a second switch S2—to the second connection A2 of the capacitance being measured CM. The non-inverting entrance of the amplifier V is located at the half operating voltage ½ UB. In addition, the integrating device I has an integrating resistor RI, which is connected by the connection 12 to the inverting entrance of the amplifier V and thus to the integrating capacitor CI. With its other connection 13, on the other hand, the integrating resistor RI is connected to a device by means of which the integrating device, i.e., the ascending and descending integration process of the integrating device I, is established. In FIG. 1 this device consists of two switches connected in series, i.e., a fourth and fifth switch S4, S5, whose series connection lies between the operating voltage UB and reference potential 10. The fourth switch S4 lies between the connection 13 of the integrating resistor RI and a terminal for the full operating voltage UB, while the other, fifth switch S5 is positioned between the connection 13 of the integrating resistor RI and the reference potential 10.

Finally, the outlet of the amplifier V and thus the outlet of the integrating device I is connected to the entrance of a comparator K, whose other entrance is connected to a reference voltage UR, which ideally will also be half the operating voltage ½ UB. On the outlet side this comparator K is connected to a control device S, which provides the first to the sixth control signals v1, v2, v3, v4, v5, and v6 for controlling the first through sixth switches S1, S2, S3, S4, S5, and S6 shown in FIG. 1.

At the outlet of the comparator K a frequency signal can be scanned whose frequency corresponds to the recharging frequency f of the integrating capacitor CI and represents a particularly direct value for the capacitance CM being measured.

The process of measuring the capacitance CM unfolds in different phases. First the capacitance CM is fully discharged by closing the first switch 1 at the first time point t1, whereupon the second, third, and sixth switches S2, S3, and S6 are opened.

The first switch S1 is then opened at the second time point t2. At the same time, or at the third time point t3, the second switch S2 is closed for a brief period of time. As a result, the capacitance CM being measured is charged by the integrating device, assuming that the fourth switch S4 is closed and the fifth switch S5 is opened. The capacitance CM being measured is consequently charged to one half the operating voltage ½ UB by the integrating capacitor CI of the integrating device I. As an alternative, or in addition, it is possible to close the sixth switch S6, in order to apply half the operating voltage UB/2.

The closing interval for the fourth time point t4 of the second switch S2 is so calculated as to permit the charging to one half the operating voltage UB/2. Tests have shown that about 0.05 (5 percent) of the cycle time T is sufficient for this. The time period, i.e., the first recharging period tk1, can equal, e.g., 10 µs.

Charging the capacitance CM being measured using the integrating capacitor or the integrating capacitance CI leads at the third time point t3 to a positive voltage jump at the outlet of the integrating amplifier V. After the capacitance CM being measured is charged, the latter's charge is equal to $$Q=CM*UB/2=CI*\Delta U.$$

From this it follows that the voltage jump $\Delta U$ at the outlet of the integrating amplifier V is equal to $$\Delta U = \frac{CM*UB/2}{CI}.$$

The reloading time tk1 is determined by the rapidity of the integrating amplifier V and of any series resistances that are present. Belonging among these series resistances, along with the switch resistances of the sixth and second switches S6, S2, is the series resistance RK of the capacitance CM being measured.

If resistances RF parallel to the capacitance CM being measured are present, they take effect only during the short recharging period, and thus during the coupling period tk1, tk2. For the descending integration a parallel resistance would lie in series with the integrating resistor RI and would thus increase the integrating time constant of the integrating device I.

Then, at the fourth time point t4, the second switch S2 is again opened, thereby uncoupling the capacitance CM being measured from the integrating device I. Due to the constrained-current operation of the integrating resistor RI into the inverting entrance of the operational amplifier V, which functions as an integrator, this leads to the discharging of the integrating capacitor CI until the reference voltage UR of the comparator K applies at the outlet A of the integrating device.

At the same time as the fourth step—or in the next or fifth step t5—the third switch S3 is closed by the third switching signal v3, and the capacitance being measured CM is thereby applied to the full operating voltage UB.

Directly at the time of the fourth time point—or after a time delay determined by a signal from the control device S, e.g., a time delay of 0.1 µs—the control device S at the fifth time point t5 guides the third control signal v3 to logical "1". Thereupon the capacitance CM and, if so desired, the additional reference capacitance are applied to the full operating voltage UB and are charged to that voltage.

From this fifth time point t5 on, the output signal A of the integrating amplifier V approximates from above the reference threshold UR for the comparator K, such that the reference threshold UR corresponds to, e.g., half the operating voltage UB/2. After the decay interval tin, beginning with the third time point t3, the voltage at the outlet of the amplifier V reaches the reference threshold UR. The interval tm (e.g. tm1, tm2) is calculated as follows:

$$tm = \frac{CM * UB/2}{CI * UB/2} * RI * CI = CM * RI.$$

At the sixth time point t6 the reference threshold UR of half the operating voltage UB/2 is reached, and at this time point the comparator output signal tips back to logical "1". Since this comparator output signal is fed to the control device S, this device S simultaneously changes the third control v3 to logical "0". Due to the coupling characteristics of the comparator K the comparator output signal remains on logical "1" directly after the sixth time point.

At the sixth time point t6 or, in time-staggered fashion, at the seventh time point t7, the control device S then once more closes the second switch S2, with the result that the capacitance being measured CM is discharged to half the operating voltage ½ UB and this discharging surge is transferred to the integrating capacitor CI as a negative charge.

To this end, the second switch S2 is also briefly closed, from the seventh time point t7 to the eighth time point t8.

The interval of time between the seventh and the eighth time point t7, t8 corresponds in turn to the switching times tk1, tk2. In keeping with basic theory, a transfer of charge therefore takes place that is identical to that described above, but with reversed signs, so that at the seventh time point t7 a negative voltage surge occurs at the integrator outlet A.

The fifth switch S5 is then closed and the fourth switch S4 opened. This causes the integrating resistor CI, via the integrating resistor RI, to return-charge the integrating capacitor CI up to the reference voltage UR, ideally half the operating voltage ½ UB.

Of particular notice is the fact that the closing period for the second switch S2 is a fixed, predetermined interval tk1, tk2. This time interval tk1, tk2 does not depend on the charging state of the integrating capacitor CI. The discharging time of the integrating capacitor CI is determined exclusively by the comparator K arriving at the reference voltage UR and by the value of the charging surge which the capacitance CM being measured imparts to the integrating capacitor CI.

Both the discharging period and the charging period of the integrating capacitor CI determine the frequency of the capacitance frequency conversion of the circuit arrangement shown in FIG. 1.

As can also be seen from FIG. 1, the second connection A2 (which is not attached to the reference potential 10) of the capacitance being measured CM can be lead outward at low resistance to a tap 4. This connection or tap 4 serves as an active guard line which makes it possible to locally relieve the evaluating circuit in the case of high-temperature versions of the measuring capacitor CM, without the measuring result being falsified by a conducting capacitance that additionally appears. Furthermore, the entrance capacitance of the integrating amplifier V cannot affect the measuring result, since the entrance of the amplifier V always remains at constant potential.

It is useful to connect the control device S to other components, e.g., a timing pulse generator C for producing a system clock pulse. The control device S releases control signals v1–v6 for the switches S1-S6 as a function of the clock signal of the pulse generator C and the frequency signal f emitted by the comparator K.

In place of the fourth and fifth switches S4, S5, which connect the integrating resistor RI to the operating voltage UB or, as the case may be, the reference voltage 10, it is possible to employ an integrating circuit which applies the output signal f of the comparator K to the integrating resistor RI by means of an inverter, as is known to the prior art from DE 43 40 472 C1. In this case, the positive entrance of the comparator K will be expediently coupled by another capacitor to that capacitor's outlet and—by another resistor—to the reference voltage, e.g., half the operating voltage UB/2.

Figure 2:
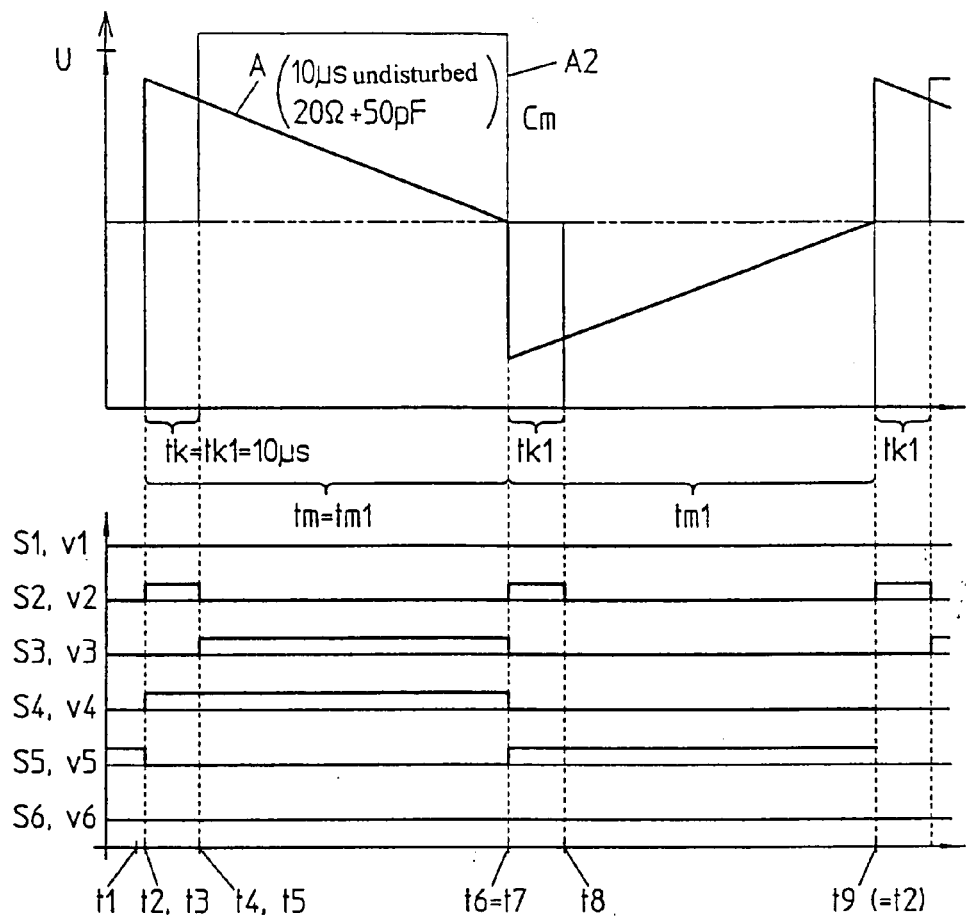
Figure 3:
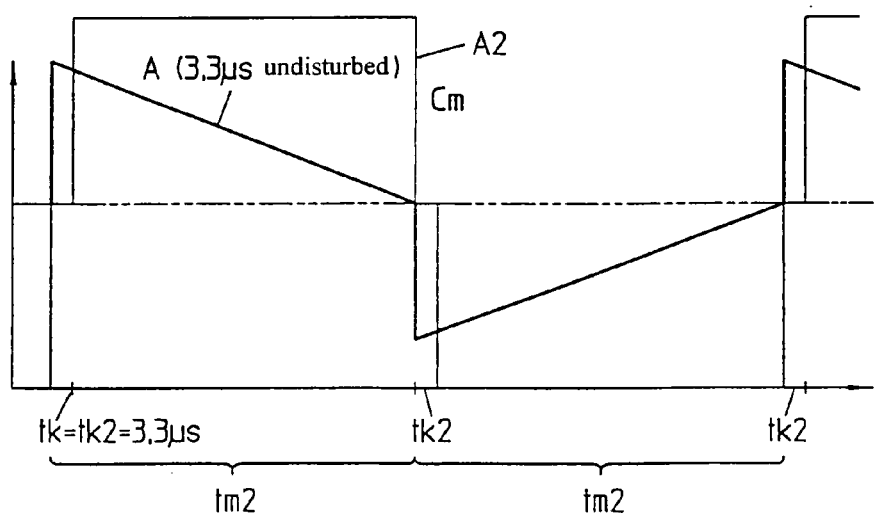

It is evident from the comparison given in FIGS. 2 and 3 that, given an ideal measuring condition at the measuring cell exhibiting the capacitance CM being measured and independent of the length of the first or second switching interval, between the third and fourth time point t3, t4, and the seventh and eighth time point t7, t8, which for the first or second recharging interval tk1, tk2 of 10 µs and 3.3 µs respectively, the integrating capacitor is completely charged, so that the discharging period between the third and sixth, or sixth and ninth time points t3–t6, t6–t9 is equally long in both cases. The frequency signal fat the outlet of the comparator K accordingly exhibits an identical period T.

The voltage state of the capacitance CM being measured is also shown in FIGS. 2 and 3; there is a central value at the closed second switch S2 during the charging period tk1 and tk2.

FIGS. 2 and 3 show the voltage curves at the measuring cell connection, or at the capacitance CM being measured, and at the integrator outlet A, for measuring periods of 10 µs and 3.3 µs. In both cases, the capacitance of the measuring capacitor is 50 pF and the effective internal resistance connected in series is 20 Ω. Ideal conditions are therefore present. The length of the measuring period remains constant for both the recharging intervals of 3.3 µs and 10 µs because the measuring capacitor, i.e., the capacitance CM being measured, is completely recharged after only 3.3 µs. The increase in the integrator outlet voltage at outlet A of the integrator I is constant and is independent of the capacitance CM being measured. The voltage jump at the integrator outlet is proportional to the value of the capacitance CM being measured. The sixth switch S6 is active when switched from the measuring capacitance to the reference capacitance. Consequently the sixth switch S6 in FIG. 2 is constantly in the opened state.

Figure 4A:
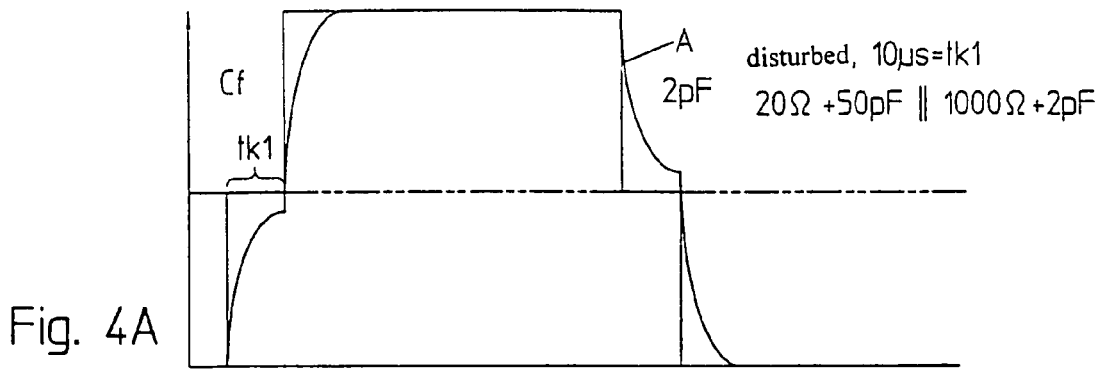
Figure 4B:
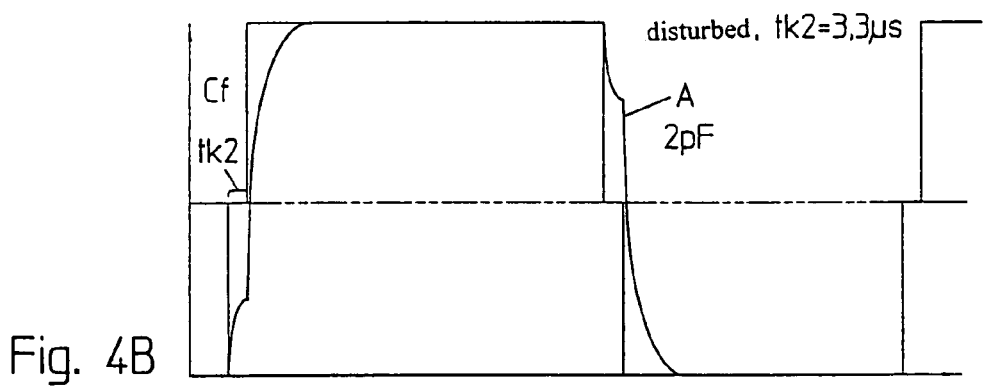

FIGS. 4A and 4B graphically depict the voltage curves at the moisture-dependent capacitance CF of 2 pF for the charging and recharging periods of 10 µs and 3.3 µs.

Figure 5A:
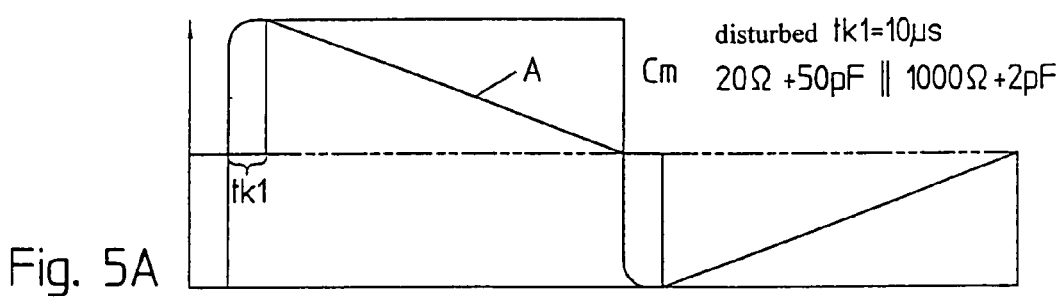
Figure 5B:
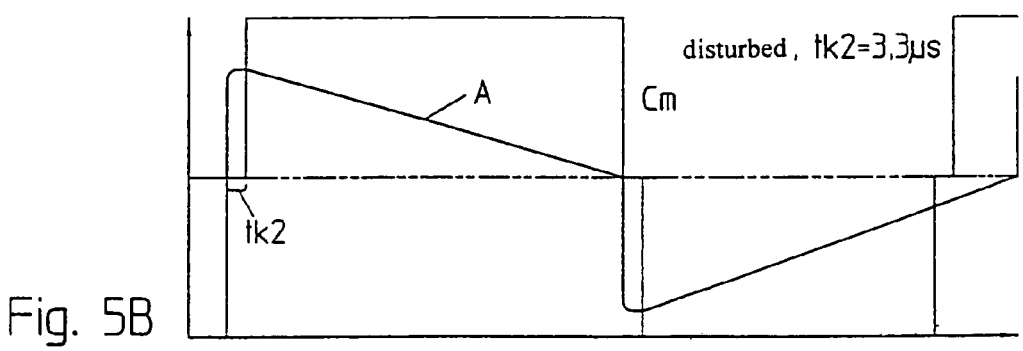

FIGS. 5A and 5B depict the time states for a non-ideal measuring condition, e.g., a moist environment around the capacitance CM being measured. For the long recharging period of 10 µs, in addition to the capacitance CK of 50 pF and the internal resistance RK of 20 Ω, there is a parallel influence at work in the interference capacitance CF=2 pF and the interference resistance RF of 1000 Ohm. As a result, the parallel measuring capacitor is almost completely recharged. A further consequence is that the measured period is increased in length, since the integrator I takes longer to return to the reference voltage UB/2=UR. The interfering parallel capacitor value DF=2 pF completely enters the measuring result via the recharging period of tk1=10 µs.

As shown in FIG. 5B, in contrast, the parallel measuring capacitor is only partly recharged for the short recharging period of 3.3 µs, so that at the integrator outlet a signal is produced which, at the outlet of the comparator K, releases a frequency signal f with a shorter period. Furthermore, a different curve becomes evident at the outlet A of the integrator I during the measuring time or recharging period tk2. Along with the modified period T, or frequency of the comparator outlet signal f, the change in the curve, as compared to the corresponding curve for the longer recharging period, must be evaluated in determining a measuring condition that changes the normal capacitance state.

Figure 6:
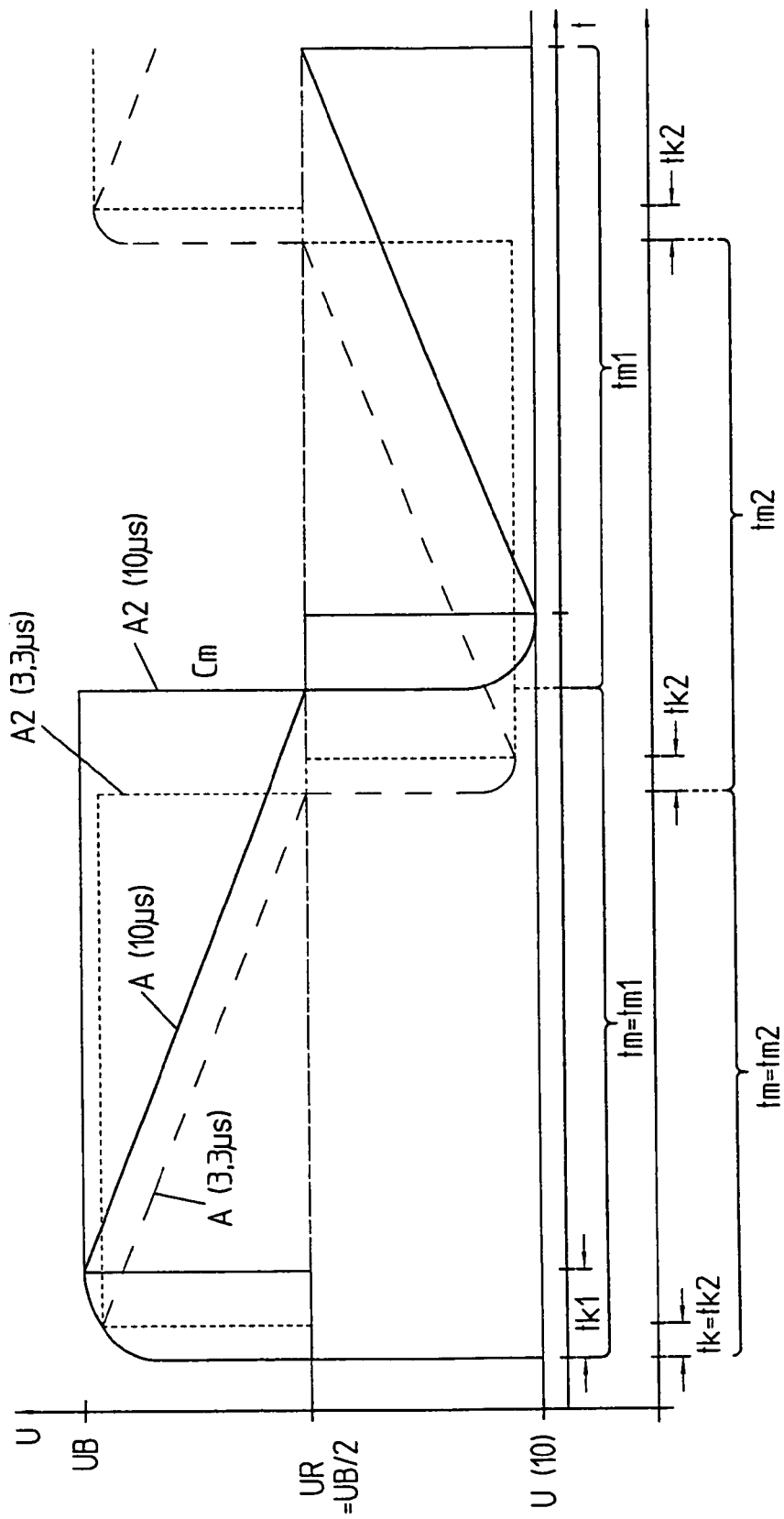

FIG. 6 directly superimposes the two curves that FIGS. 5A and 5B distort for the sake of a more graphic depiction, in the case of a disturbed capacitance being measured CM in the case of the two different recharging periods tk1, tk2. The figure makes evident the shorter time for the shorter recharging period.

The invention claimed is:

1. A process for evaluating a measuring device comprising a capacitor (CM), the process comprising:
    charging the capacitor over a first charging period (tk1),
    determining the charge of the capacitor as a function of a first measured value (tm1),
    charging the capacitor over a second charging period (tk2), which is different from the first charging period (tk1),
    determining the charge of the capacitor as a function of a second measured value (tm2), and
    comparing the first and the second measured values (tm1, tm2) to reach a comparative result for determining a measuring condition that changes the normal state of the capacitor.

2. A process according to claim 1, in which the capacitor (CM) is charged by recharging from or to another capacitor (CI), specifically an integrating capacitor, proceeding from a reference voltage value (UB/2).

3. A process according to claim 2, in which after the recharging process the other capacitor (CI) is discharged in linear fashion or is return-charged until the reference voltage value (UB/2) is reached.

4. A process according to claim 2, in which the period of discharging or return-charging is established as the first or second measured value (tm1, tm2).

5. A process according to claim 2, in which the period (tm1, tm2) of discharging or return-charging, inclusive of the recharging period (tk1 or tk2), is determined as the first or second measured value (tm1, tm2).

6. A process according to claim 2, in which the other capacitor (CI) is located in an integrating circuit (I) for linear charging or discharging up to a reference voltage value (UB/2).

7. A process according to claim 1, in which the first and second charging periods (tk1, tk2) are so chosen that equal or comparable measured values will be only be produced under selected measuring conditions.

8. A process according to claim 7, in which the longer of the first or, as the case may be, the second charging period (tk1, tk2) is so chosen that the capacitor (CM) is charged completely or up to a minimum charging value in both dry and moist capacitor surroundings, and the second charging period (tk2) is so chosen that the capacitor (CM) is charged completely or up to a minimum charging value only when its surroundings are moist.

9. A process according to claim 1, in which the comparative result is compared with a tolerance value.

10. A process according to claim 1, in which the comparative result is compared with pre-selectable value ranges to ascertain an amount of change in the measuring condition.

11. A process according to claim 1, in which a signal is released when the comparative result exceeds or falls short of a predetermined limit value, specifically, such that a correction is made for the measuring condition of the given capacitor.

12. A process according to claim 1, in which a difference between the measured values (tm1, tm2) is used to ascertain a moisture-determined change in capacitance as a measured condition.

13. A process according to claim 1, in which a difference between the measured values (tm1, tm2) indicates a change in the internal resistances of a capacitor charging path.

14. A process according to claim 1, in which the capacitor (CM), which is connected to the reference potential (10) by an initial connection (A1), is measured using an integrating device (I) connected to a reference voltage (UB), such that the integrating capacitor (CI) is charged with a charge located on the capacitor (CM) being measured and is then discharged, and the recharging (f) that then arises represents a measure of the capacitor (CM) being investigated, and such that the integrating capacitor (CI) is in each case charged and discharged up to a predetermined reference threshold, and, by coupling the capacitors, negative or positive charging surges, particularly of the same amplitude, are transferred to the integrating capacitor (CI), as second capacitor, at the beginning of the charging or discharging process.

15. A circuit arrangement for implementing a process according to claim 1, comprising:
    a capacitor (CM),
    a charging and discharging circuit arrangement (LE, S) for charging and discharging the capacitor (CM),
    a measured value determinator (S) for determining a measured value (tm1, tm2), and
    an evaluating device (S) for evaluating the measured value (tm1, tm2), wherein
    the charging and discharging arrangement (LE, S) is designed to charge and discharge the capacitance (CM) with at least two different charging periods (tk1, tk2),
    the measured value determinator (S) is designed to determine at least two corresponding measured values (tm1, tm2), and
    the evaluating device (S) is designed to compare the measured values (tm1, tm2) which were produced and ascertained over two different charging periods (tk1, tk2), in order to determine a change in the measuring conditions of the capacitor (CM).

16. A circuit arrangement according to claim 15, in which the charging and discharging circuit arrangement (LE, S) is designed as a recharging device (S1–S6) for recharging between the capacitor (CM) and a second capacitor (CI) over the period for charging or discharging (tk1, tk2).

17. A circuit arrangement according to claim 15, in which the discharging and discharging circuit arrangement (S1–S6) exhibits an integrating circuit (I), to and from which the charge of the capacitor (CM) is directed.

18. A circuit arrangement according to claim 15 with
    the capacitor (CM) being measured, with a first connection (A1) set at the reference potential (10) and with a second connection (A2),
    an integrating device (I) with an integrating capacitor as the second capacitor (CI),
    an intitial switching device (S2) to connect the second connection (A2) of the capacitor (CM) being measured to the integrating device (I),
    a device (S4, S5, K, S) for establishing the ascending and descending integration process of the integrating device (I), a charging/discharging device (LE, S1, S3, S6) for the capacitor (CM) being measured and for the integrating capacitor (CI), and a control device (S) for controlling the first switching device (S2) of the device (S4, S5) for establishing the ascending and descending integration process of the integrating device and of the charging/discharging device (S1, S3, S6), in such a way that the integrating capacitor (CI) is in each case charged and discharged up to a predetermined reference threshold and at the beginning of the charging or discharging process the capacitor (CM) is coupled, with the result that a negative or positive charging surge, and specifically surges of equal amplitude, is transferred to the integrating capacitor.

* * * * *